United States Patent
Charrier et al.

(10) Patent No.: US 7,959,687 B2
(45) Date of Patent: Jun. 14, 2011

(54) HAIR DYEING PROCESS COMPRISING A POST-TREATMENT USING AT LEAST ONE ORGANIC SILICON COMPOUND

(75) Inventors: Delphine Charrier, Paris (FR); Marie-Pascale Audousset, Asnieres (FR); Leïla Hercouet, Neuilly Plaisance (FR)

(73) Assignee: L'Oreal, S.A. (FR)

( * ) Notice: Subject to any disclaimer, the term of this patent is extended or adjusted under 35 U.S.C. 154(b) by 0 days.

(21) Appl. No.: 12/769,962

(22) Filed: Apr. 29, 2010

(65) Prior Publication Data

US 2010/0275945 A1    Nov. 4, 2010

Related U.S. Application Data

(60) Provisional application No. 61/179,839, filed on May 20, 2009.

(30) Foreign Application Priority Data

Apr. 30, 2009   (FR) ...................................... 09 52913

(51) Int. Cl.
*A61Q 5/10* (2006.01)
(52) U.S. Cl. ............. 8/405; 8/406; 8/408; 8/410; 8/411; 8/412; 8/504; 8/581; 8/632; 132/202; 132/208
(58) Field of Classification Search ............. 8/405, 406, 8/408, 410, 411, 412, 504, 581, 632; 132/202, 132/208
See application file for complete search history.

(56) References Cited

U.S. PATENT DOCUMENTS

| 6,824,765 B2 | 11/2004 | Gawtrey et al. |
| 6,953,572 B1 | 10/2005 | Samain et al. |
| 6,953,584 B1 | 10/2005 | Samain et al. |
| 2009/0291058 A1* | 11/2009 | Woodland et al. ......... 424/70.28 |

FOREIGN PATENT DOCUMENTS

| EP | 1 312 346 A2 | 5/2003 |
| EP | 1 767 187 A2 | 3/2007 |
| EP | 1 767 189 A2 | 3/2007 |
| FR | 2 783 164 A1 | 3/2000 |
| WO | WO 01/22925 A1 | 4/2001 |
| WO | WO 01/22931 A1 | 4/2001 |
| WO | WO 2006/118942 A2 | 11/2006 |

OTHER PUBLICATIONS

STIC Search Report dated Sep. 29, 2010.*
French Search Report for FR 0952913, dated Dec. 15, 2009.
English language abstract of EP 1 767 187 A2, Mar. 28, 2007.
English language abstract of EP 1 767 189 A2, Mar. 28, 2007.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure relates to a hair dyeing process comprising dyeing the hair by applying to the hair at least one dyeing composition comprising at least one dye precursor; rinsing the hair; and post-treating the hair by applying to the hair at least one aqueous composition comprising at least 30% of water and at least 20% of at least one organic silicon compound chosen from the silanes that comprise one silicon atom and the siloxanes that comprise two or three silicon atoms, wherein the least one organic silicon compound also comprises at least one basic chemical functional group and at least one hydroxyl group or hydrolysable group per molecule.

20 Claims, No Drawings

HAIR DYEING PROCESS COMPRISING A POST-TREATMENT USING AT LEAST ONE ORGANIC SILICON COMPOUND

This application claims benefit of U.S. Provisional Application No. 61/179,839, filed May 20, 2009. This application also claims benefit of priority under 35 U.S.C. §119 to French Patent Application No. 0952913, filed Apr. 30, 2009.

The present disclosure relates to a hair dyeing process comprising a post-treatment that uses at least one organic silicon compound.

The hair may generally become damaged and embrittled by the action of external atmospheric agents, such as light and bad weather, and by mechanical or chemical treatments, such as brushing, combing, bleaching, perming, and/or dyeing. The result of this is that the hair may be difficult to manage, for example it may be difficult to disentangle or to style, and heads of hair, even thick heads of hair, may have difficultly, for example, in maintaining an attractive style due to the fact that the hair may lack vigour, volume, and liveliness.

This degradation of the properties of the hair may furthermore be increased by permanent hair dyeing treatments, which consist in applying to the hair at least one dye precursor such as oxidation bases and couplers and an oxidizing agent. These precursors, under the action of the oxidizing agent, will form at least one colored species in the hair.

At the same time, it has been observed that consumers may seek compositions that make it possible not only to dye the hair satisfactorily but also to achieve satisfactory styling effects.

For example, people who have fine or curly hair may generally seek a styling effect that gives weight, body, and volume to fine hair and defined shape to the curls of wavy hair.

It is customary to apply, after dyeing, hair conditioning products that make it possible to provide disentangling and to improve the feel, but these products may not sufficiently provide styling effects, for example in terms of body, weight, or volume.

There may therefore be a need for a permanent hair dyeing process with dye precursors such as oxidation bases and couplers, which does not have the drawbacks described above, that is to say that may result in sufficient styling effects, for example in terms of body, weight, or volume with, in addition, a resistance of these effects to shampoos and to external attacking factors with good cosmetic properties, irrespective of the sensitization of the treated hair.

The present disclosure therefore provides a hair dyeing process that may make it possible to satisfactorily dye the hair with, in the end, a sufficient and durable styling effect.

Disclosed herein is a hair dyeing process comprising:
dyeing the hair by a process comprising
applying to the hair at least one dyeing composition comprising at least one dye precursor, and;
rinsing the hair; and
post-treating the hair by a process comprising
applying to the hair at least one aqueous composition comprising at least 30% of water and at least 20% of at least one organic silicon compound chosen from the silanes that comprise one silicon atom and the siloxanes that comprise two or three silicon atoms, wherein the at least one organic silicon compound also comprises at least one basic chemical functional group and at least one hydroxyl group or hydrolysable group per molecule.

The disclosed process may make it possible to obtain a coloring of the hair with satisfactory dyeing properties including, for example, intensity, chromaticity, selectivity, and/or good resistance of the color to external agents such as resistance to shampoos, to sweat, and/or to bad weather while giving the hair style, weight, and body.

The at least one organic silicon compound used in the at least one aqueous composition according to the disclosure is chosen from organosilanes comprising one silicon atom and organosiloxanes comprising two or three silicon atoms, for example two silicon atoms. It must, in addition, comprise at least one basic chemical functional group, such as a single basic chemical functional group. The at least one basic chemical functional group may correspond to any functional group that confers a basic character on the silicon compound and is for example an amine functional group such as a primary, secondary, or tertiary amine functional group. The at least one basic chemical functional group of the at least one organic silicon compound according to the process disclosed herein may optionally comprise other functional groups, such as, for example, another amine functional group, an acid functional group, or a halogen functional group.

The at least one organic silicon compound used in the at least one aqueous composition according to the process disclosed herein also comprises at least one hydrolysable or hydroxyl group per molecule. The at least one hydrolysable group may, for example, be chosen from alkoxy, aryloxy, and halogen groups. It may also, optionally, comprise other chemical functional groups such as acid functional groups.

According to at least one embodiment, the at least one organic silicon used in the at least one aqueous composition according to the disclosure are chosen from those of formula (I):

wherein:
R4 represents a halogen or an OR' or R'1 group;
R5 represents a halogen or an OR" or R'2 group;
R6 represents a halogen or an OR''' or R'3 group;
R1, R2, R3, R', R", R''', R'2, and R'3 represent, independently of one another, a saturated or unsaturated, linear or branched hydrocarbon-based group optionally bearing additional chemical groups, R1, R2, R', R", and R''' optionally being hydrogen and at least two of the groups R4, R5, and R6 respectively denoting OR', OR" and OR''', at least two of the groups R', R", and R''' being other than hydrogen.

In at least one embodiment, the groups $R_1$, $R_2$, R', $R'_1$, $R'_2$, $R'_3$, R", and R''' are chosen from $C_1$-$C_{12}$ alkyl, $C_6$ to $C_{14}$ aryl, ($C_1$ to $C_8$)alkyl($C_6$ to $C_{14}$)aryl, and ($C_6$ to $C_{14}$)aryl($C_1$ to $C_8$)alkyl radicals.

According to at least one embodiment, the at least one organosiloxane used in the at least one aqueous composition according to the process disclosed herein are chosen from those of formula (II):

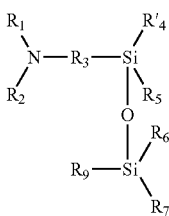

wherein:

R1, R2, R3, R5, and R6 are defined as above;

R'4 represents a halogen atom or an OR11 group;

R7 represents a halogen atom or an OR10 or R"1 group;

R9 represents a halogen atom or an OR8, R"2, or R3NR1R2 group;

R"1, R"2, R8, R10, and R11 represent a saturated or unsaturated, linear or branched hydrocarbon-based group optionally bearing additional chemical groups, the groups R11, R10, and R8 optionally representing a hydrogen atom; at least one of the groups R6, R7, and R9 denoting a halogen atom or an OR'", $OR_{10}$, or $OR_8$ group.

In at least one embodiment, the groups $R"_1$, $R"_2$, $R_8$, $R_{10}$ and $R_{11}$ are chosen from $C_1$-$C_{12}$ alkyl, $C_6$ to $C_{14}$ aryl, ($C_1$ to $C_8$)alkyl($C_6$ to $C_{14}$)aryl, and ($C_6$ to $C_{14}$)aryl($C_1$ to $C_8$)alkyl radicals.

In at least one embodiment, the halogen atom is a chlorine atom.

The at least one organic silicon compound used in the at least one aqueous composition according to the process disclosed herein may for example be chosen from those of formula (III):

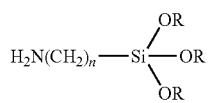

wherein the R radicals, which are identical or different, are chosen from $C_1$-$C_6$, such as $C_1$-$C_2$, alkyl radicals and n is an integer chosen from 1 to 6, such as chosen from 2 to 4.

In at least one embodiment, the at least one organic silicon compound is soluble in water. In certain embodiments, the least one organic silicon compound is soluble at a concentration of 2% by weight, for example at a concentration of 5% by weight, and for example at a concentration of 10% by weight in water at the temperature of 25° C.±5° C. and at atmospheric pressure. The term "soluble" is understood to mean the formation of a single macroscopic phase.

In at least one embodiment, the at least one organic silicon compound present in the at least one aqueous composition according to the process disclosed herein is (3-aminopropyl) triethoxysilane.

The at least one organic silicon compound can be present in the at least one aqueous composition in an amount ranging, for example, from 20% to 65% by weight, such as from 30% to 60% by weight, and from 40% to 50% by weight, relative to the total weight of the at least one aqueous composition.

According to at least one embodiment, the water is present in the at least one aqueous composition in an amount ranging from 30% to 78% by weight, for instance from 40% to 70% by weight, such as from 45% to 60% by weight, relative to the total weight of the at least one aqueous composition.

The at least one organic silicon compound can be partially neutralized via use of a neutralizing agent or pH regulator, so that the neutralization reaches 1/1000 to 99/100, such as 0.2/100 to 70/100. For example, the neutralization may be 0.2/100 to 60/100.

The pH regulators may be any acids or mixtures of acids that are cosmetically acceptable and soluble in the medium of the composition. Among the acids that can be used, non-limiting mention may be made of hydrochloric acid, phosphoric acid, sulphonic acid, and organic acids. The at least one aqueous composition used according to the disclosure may also contain at least one other organic acid.

The at least one organic acid is generally chosen from acids comprising at least one carboxylic, sulphonic, phosphonic, or phosphoric acid functional group. It may contain other chemical functional groups, for example hydroxyl or amino functional groups. It may be saturated or unsaturated. Non-limiting mention may for example be made of acetic acid, propanoic acid, butanoic acid, lactic acid, glycolic acid, ascorbic acid, maleic acid, phthalic acid, succinic acid, taurine, tartaric acid, gluconic acid, glucuronic acid, and citric acid. For example, the organic acids lactic acid, acetic acid, and citric acid may be used.

In the post-treatment process, the at least one aqueous composition comprising the at least one organic silicon compound generally has a pH ranging in value from 2 to 13, such as from 4 to 11. For instance, the pH of the at least one aqueous composition obtained with the pH regulator may range in value from 6 to 11, such as from 8 to 10.

The at least one aqueous composition containing the at least one organic silicon compound may, in addition, contain at least one thickener. The at least one thickening agent may be chosen from fatty acid amides (coconut diethanolamide or monoethanolamide, oxyethylenated alkylether carboxylic acid monoethanolamide), cellulose-based thickeners (hydroxyethyl cellulose, hydroxypropyl cellulose, carboxymethyl cellulose), guar gum and derivatives thereof (hydroxypropyl guar), gums of microbial origin (xanthan gum, scleroglucan gum), or crosslinked homopolymers or acrylic acid or of acrylamidopropanesulphonic acid.

The at least one hair dyeing composition comprises at least one dye precursor chosen from at least one oxidation base and/or at least one coupler.

The at least one oxidation base is chosen from those conventionally known in oxidation dyeing, and among which non-limiting mention may for example be made of ortho-phenylenediamines and para-phenylenediamines, double bases, ortho-aminophenols and para-aminophenols, heterocyclic bases, and the addition salts thereof with an acid.

The at least one oxidation base may, for example, be cationic.

The para-phenylenediamines can be chosen for example from those of the formula (IV) below and the addition salts thereof with an acid:

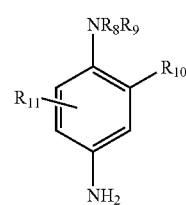

wherein:
R$_8$ represents a hydrogen atom, a C$_1$-C$_4$ alkyl radical, a C$_1$-C$_4$ monohydroxyalkyl radical, a C$_2$-C$_4$ polyhydroxyalkyl radical, a (C$_1$-C$_4$)alkoxy(C$_1$-C$_4$)alkyl radical, a C$_1$-C$_4$ alkyl radical substituted by a nitrogenous group, a phenyl radical, or a 4'-aminophenyl radical;
R$_9$ represents a hydrogen atom, a C$_1$-C$_4$ alkyl radical, a C$_1$-C$_4$ monohydroxyalkyl radical, a C$_2$-C$_4$ polyhydroxyalkyl radical, a (C$_1$-C$_4$)alkoxy(C$_1$-C$_4$)alkyl radical, or a C$_1$-C$_4$ radical substituted by a nitrogenous group;
R$_8$ and R$_9$ can also form, with the nitrogen atom which bears them, a 5- or 6-membered nitrogenous heterocycle optionally substituted by at least one alkyl, hydroxyl, or ureido group;
R$_{10}$ represents a hydrogen atom, a halogen atom, such as a chlorine atom, a C$_1$-C$_4$ alkyl radical, a sulpho radical, a carboxyl radical, a C$_1$-C$_4$ monohydroxyalkyl radical, a C$_1$-C$_4$ hydroxyalkoxy radical, a C$_1$-C$_4$ acetylaminoalkoxy radical, a C$_1$-C$_4$ mesylaminoalkoxy radical, or a C$_1$-C$_4$ carbamoylaminoalkoxy radical; and
R$_{11}$ represents a hydrogen atom, a halogen atom, or a C$_1$-C$_4$ alkyl radical.

Non-limiting mention may for example be made, among the nitrogenous groups of the formula (IV) above, of the amino, mono(C$_1$-C$_4$)alkylamino, di(C$_1$-C$_4$)alkylamino, tri (C$_1$-C$_4$)alkylamino, monohydroxy(C$_1$-C$_4$)alkylamino, imidazolinium, and ammonium radicals.

Non-limiting mention may for example be made, among the para-phenylenediamines of formula (IV) above, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine, and the addition salts thereof with an acid.

Non-limiting mention may also for example be made, among the para-phenylenediamines of formula (IV) above, to para-phenylenediamine, para-toluoylenediamine, 2-isopropyl-para-phenylenediamine, 2-(β-hydroxyethyl)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and the addition salts thereof with an acid.

In certain examples, the para-phenylenediamines of formula (IV) can be chosen from para-phenylenediamine, para-toluoylenediamine, N,N-bis(β-hydroxyethyl)-para-phenylenediamine and the addition salts thereof with an acid.

In the context of the disclosure, the expression "double bases" is understood to mean the compounds comprising at least two aromatic rings on which amino and/or hydroxyl groups are borne.

Non-limiting mention may for example be made, among the double bases, of those of the formula (V) below and the addition salts thereof with an acid:

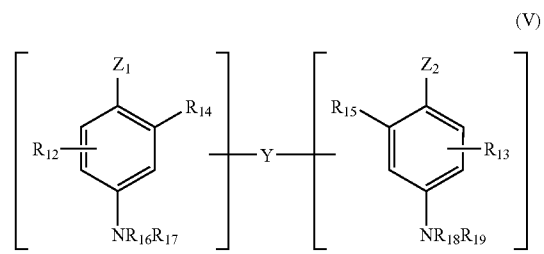

wherein:
Z$_1$ and Z$_2$, which are identical or different, represent a hydroxyl or —NH$_2$ radical which can be substituted by a C$_1$-C$_4$ alkyl radical or by a linker Y;
the linker Y represents a linear or branched alkylene chain comprising from 1 to 14 carbon atoms which can be interrupted or terminated by at least one nitrogenous group and/or by at least one heteroatom, such as oxygen, sulphur or nitrogen atoms, and which is optionally substituted by at least one hydroxyl or C$_1$-C$_6$ alkoxy radical;
R$_{12}$ and R$_{13}$ represent a hydrogen or halogen atom, a C$_1$-C$_4$ alkyl radical, a C$_1$-C$_4$ monohydroxyalkyl radical, a C$_2$-C$_4$ polyhydroxyalkyl radical, a C$_1$-C$_4$ aminoalkyl radical, or a linker Y;
R$_{14}$, R$_{15}$, R$_{16}$, R$_{17}$, R$_{18}$, and R$_{19}$, which are identical or different, represent a hydrogen atom, a linker Y, or a C$_1$-C$_4$ alkyl radical; and
it being understood that the compounds of formula (V) only comprise a single linker Y per molecule.

Non-limiting mention may for example be made, among the nitrogenous groups of the formula (V) above, of the amino, mono(C$_1$-C$_4$)alkylamino, di(C$_1$-C$_4$)alkylamino, tri (C$_1$-C$_4$)alkylamino, monohydroxy(C$_1$-C$_4$)alkylamino, imidazolinium, and ammonium radicals.

Non-limiting mention may for example be made, among the double bases of formula (V) above, of N,N'-bis(β-hydroxyethyl)-N,N'-bis(4'-aminophenyl)-1,3-diamino-propanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylene-diamine, N,N'-diethyl-N,N'-bis(4'-amino-3'-methylphenyl)ethylenediamine, 1,8-bis(2,5-diaminophenoxy)-3,5-dioxaoctane, and the addition salts thereof with an acid.

N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid may for example be mentioned among the double bases of formula (V).

The para-aminophenols can be chosen for example from those of formula (VI) below and the addition salts thereof with an acid:

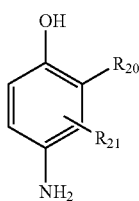

(VI)

wherein:

$R_{20}$ represents a hydrogen atom, a halogen atom, such as fluorine, a $C_1$-$C_4$ alkyl radical, a $C_1$-$C_4$ monohydroxyalkyl radical, a ($C_1$-$C_4$)alkoxy($C_1$-$C_4$)alkyl radical, a $C_1$-$C_4$ aminoalkyl radical, or a hydroxy($C_1$-$C_4$)alkylamino($C_1$-$C_4$)alkyl radical; and $R_{21}$ represents a hydrogen atom, a halogen atom, such as fluorine, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, a $C_1$-$C_4$ cyanoalkyl radical, or a ($C_1$-$C_4$)alkoxy($C_1$-$C_4$)alkyl radical.

Non-limiting mention may for example be made, among the para-aminophenols of formula (VI) above, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)-phenol, 4-amino-2-[(β-hydroxyethyl)aminomethyl]phenol and the addition salts thereof with an acid.

Para-aminophenol and 4-amino-3-methylphenol may for example be used.

The ortho-aminophenols may for example be chosen from 2-aminophenol, 2-amino-1-hydroxy-5-methylbenzene, 2-amino-1-hydroxy-6-methylbenzene, 5-acetamido-2-aminophenol and the addition salts thereof with an acid.

Non-limiting mention may for example be made, among the heterocyclic bases of pyridine derivatives, pyrimidine derivatives, pyrazole derivatives, and the addition salts thereof with an acid.

Non-limiting mention may for example be made, among pyridine derivatives, of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine, and the addition salts thereof with an acid.

Non-limiting mention may for example be made, among pyrimidine derivatives, of the compounds described, for example, in German patent DE 2 359 399 or Japanese patents JP 88-169 571 and JP 91-10659 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives, such as those mentioned in patent application FR-A-2 750 048 and among which non-liming mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and the addition salts thereof and the tautomeric forms thereof, when a tautomeric equilibrium exists.

Non-limiting mention may for example be made, among pyrazole derivatives, of the compounds described in patents DE 3 843 892 and DE 4 133 957 and patent applications WO 94/08969, WO 94/08970, FR-A-2 733 749 and DE 195 43 988, for instance 4,5-diaminopyrazoles such as, for example, 4,5-diamino-1-methylpyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole; 3,4-diaminopyrazole; 4-amino-1,3-dimethyl-5-hydrazinopyrazole; 3,4,5-triaminopyrazoles such as, for example, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole; and the addition salts thereof with an acid.

In at least one embodiment, use may be made of a 4,5-diaminopyrazole and for example of 4,5-diamino-1-(β-hydroxyethyl)pyrazole and/or one of its salts.

By way of pyrazole derivatives, non-limiting mention may also be made of diamino-N,N-dihydropyrazolopyrazolones and for example those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or an addition salt thereof may for example be used.

As heterocyclic bases, 4,5-diamino-1-(β-hydroxyethyl)pyrazole and/or 2,3-diamino-6,7-dihydro-1H,5H-pyrazolo[1,2-a]pyrazol-1-one and/or an addition salt thereof may for example be used.

As cationic oxidation bases, non-limiting mention may, for example, be made of the following compounds: para-phenylenediamines as described, for example, in patent applications FR-A-2 766 177 and FR-A-2 766 178, para-aminophenols as described, for example, in patent applications FR-A-2 766 177 and FR-A-2 766 178, ortho-phenylenediamines as described, for example, in patent applications FR-A-2 782 718, FR-A-2 782 716 and FR-A-2 782 719, ortho-aminophenols or double bases which are cationic, such as derivatives of bis(aminophenyl)alkylenediamine type, described in patent application FR-A-2 766 179, and also cationic heterocyclic bases, these compounds bearing at least one quaternary nitrogen atom.

In at least one embodiment, the cationic oxidation bases are cationic para-phenylenediamines.

In another embodiment, one variant consists in using cationic oxidation bases of para-phenylenediamine structure, at least one of the amine functional groups of which is a tertiary amine bearing a pyrrolidine ring, the molecule having at least one quaternized nitrogen atom. Such bases are, for example, described in document EP-A-1 348 695.

In at least one embodiment, the at least one dyeing composition comprises at least one oxidation base present in a total amount ranging from 0.0005% to 12% by weight, relative to the total weight of the at least one dyeing composition. For example, the at least one oxidation base may be present in a total amount ranging from 0.005% to 8% by weight, such as from 0.05% to 5% by weight, relative to the total weight of the at least one dyeing composition.

The at least one coupler may be chosen from those conventionally used in oxidation dyeing compositions, i.e. meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

The at least one coupler may for example be chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, β-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

The at least one dyeing composition may generally comprise at least one coupler present in an amount ranging from 0.0001% to 15% by weight, relative to the total weight of the at least one dyeing composition. For example, the at least one coupler may be present in an amount ranging from 0.001% to 10% by weight, such as from 0.01% to 8% by weight, relative to the total weight of the at least one dyeing composition.

The at least one oxidation base and/or at least one coupler may be present in the at least one dyeing composition disclosed herein in the form of addition salts, and for example in the form of addition salts with an acid.

The addition salts with an acid that can be used in the context of the process disclosed herein may for example be chosen from hydrochlorides, hydrobromides, sulphates, citrates, succinates, tartrates, lactates, acetates, alkyl sulphates, and alkyl sulphonates.

When the at least one oxidation base and/or the at least one coupler contain at least one carboxylic acid or sulphonic acid functional group, addition salts with a base can be envisaged. The addition salts with a base that can be used in the context of the at least one dyeing composition disclosed herein may then be for example those obtained with sodium hydroxide, potassium hydroxide, aqueous ammonia, or amines.

According to at least one embodiment of the process disclosed herein, the at least one dyeing composition comprises at least one oxidation base and at least one coupler.

According to another embodiment, the at least one dyeing composition further comprises at least one cationic polymer, the cationic charge density of which is greater than or equal to 4 milliequivalents per gram (meq/g), for example greater than or equal to 5 milliequivalents per gram (meq/g), such as ranging from 5 to 20 meq/g, such as from 5.5 to 10 meq/g.

The cationic charge density of a polymer corresponds to the number of moles of cationic charges per unit of mass of polymer under conditions in which the polymer is totally ionized. It may be determined by calculation if the structure of the polymer is known, i.e., the structure of the monomers constituting the polymer and their molar or weight proportion. It may also be determined experimentally via the Kjeldahl method, generally at a pH of about 7 at room temperature.

The at least one cationic polymer that has a cationic charge density of greater than 4 meq/g may be chosen from all those already known per se as improving the cosmetic properties of the hair treated with compositions, i.e. for example those described in European patent application EP-A-0 337 354 and in French patent applications FRA 2 270 846, FR 2 383 660, FR 2 598 611, FR 2 470 596, and FR 2 519 863.

In general, for the purposes of the present disclosure, the expression "cationic polymer" denotes any polymer comprising cationic groups and/or groups that may be ionized into cationic groups.

The at least one cationic polymer is chosen from those containing units comprising primary, secondary, tertiary, and/or quaternary amine groups that either may form part of the main polymer chain or may be borne by a side substituent directly attached thereto.

The at least one cationic polymer used generally has a number-average molecular weight ranging from 500 to $5 \times 10^6$, such as from $10^3$ to $3 \times 10^6$.

Among the cationic polymers, non-limiting mention may for example be made of polymers of the polyamine, polyaminoamide, and polyquaternary ammonium type. These are known products.

Among these polymers, non-limiting mention may be made of polymers from families (1), (2), (3), (4) and (5) listed below.

Family (1) polymers include homopolymers or copolymers derived from acrylic or methacrylic esters or amides and comprising at least one of the units of the following formulae:

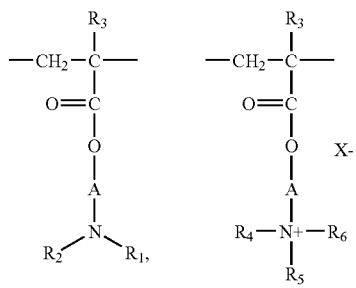

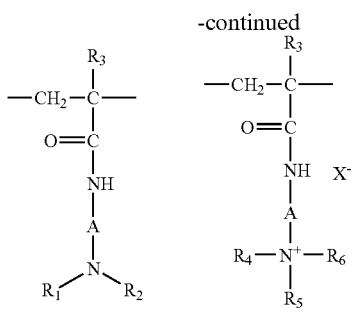

wherein:

R3, which may be identical or different, denote a hydrogen atom or a CH3 radical; A, which may be identical or different, represent a linear or branched alkyl group of 1 to 6 carbon atoms, for example 2 or 3 carbon atoms, or a hydroxyalkyl group of 1 to 4 carbon atoms;

R4, R5, and R6, which may be identical or different, represent an alkyl group having from 1 to 18 carbon atoms or a benzyl radical and for example an alkyl group having from 1 to 6 carbon atoms;

R1 and R2, which may be identical or different, represent hydrogen or an alkyl group having from 1 to 6 carbon atoms, and for example methyl or ethyl; and X denotes an anion derived from a mineral or organic acid, for example a methosulphate anion or a halide, such as chloride or bromide.

The copolymers of family (1) can also contain at least one unit derived from comonomers that may be chosen from the family of acrylamides, methacrylamides, diacetone acrylamides, acrylamides, and methacrylamides substituted on the nitrogen with lower ($C_1$-$C_4$)alkyls, acrylic or methacrylic acids or esters thereof, vinyllactams such as vinylpyrrolidone or vinylcaprolactam, and vinyl esters.

Thus, among these copolymers of family (1), non-limiting mention may be made of:

the copolymers of acrylamide and of dimethylaminoethyl methacrylate quaternized with dimethyl sulphate or with a dimethyl halide, the copolymers of acrylamide and of methacryloyloxyethyltrimethylammonium chloride described, for example, in patent application EP-A-080 976, the copolymers of acrylamide and of methacryloyloxyethyltrimethylammonium methosulphate, quaternized or non-quaternized vinylpyrrolidone/dialkylaminoalkyl acrylate or methacrylate copolymers. These polymers are described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, and crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, for example methylenebisacrylamide. A crosslinked acrylamide/methacryloyl-oxyethyltrimethylammonium chloride copolymer (20/80 by weight) in the form of a dispersion comprising 50% by weight of said copolymer in mineral oil can be used for example. This dispersion is sold under the name SALCARE® SC 92 by the company Ciba. A crosslinked methacryloyloxyethyltrimethylammonium chloride homopolymer comprising about 50% by weight of the homopolymer in mineral oil or in a liquid ester can also be used. These dispersions are sold under the names SALCARE® SC 95 and SALCARE® SC 96 by the company Ciba.

Family (2) polymers include cyclopolymers of alkyldiallylamine or of dialkyl-diallylammonium, such as the homopolymers or copolymers comprising, as main constituent of the chain, units corresponding to the formulae (VII) or (VIII):

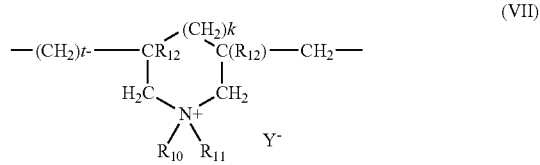 (VII)

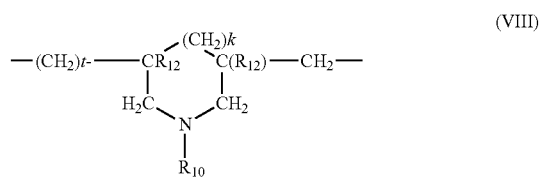 (VIII)

wherein k and t are equal to 0 or 1, the sum k+t being equal to 1; $R_{12}$ denotes a hydrogen atom or a methyl radical; $R_{10}$ and $R_{11}$, independently of one another, denote an alkyl group having from 1 to 6 carbon atoms, a hydroxyalkyl group wherein the alkyl group for example has 1 to 5 carbon atoms, a lower ($C_1$-$C_4$) amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described for example in French patent 2 080 759 and in its Certificate of Addition 2 190 406.

In certain embodiments, $R_{10}$ and $R_{11}$, independently of one another, for example denote an alkyl group having from 1 to 4 carbon atoms.

Among the polymers defined above, non-limiting mention may for example be made of the homopolymers of dimethyldiallylammonium salts (for example, chloride) sold for example under the name MERQUAT 100 by the company Nalco (and its homologues of low weight-average molar mass) and diallyldimethylammonium chloride/acrylamide copolymers.

Family (3) polymers include quaternary copolymers of vinyllactam (vinylpyrrolidone and/or vinylcaprolactam) and of vinylimidazole.

Family (4) polymers include the quaternary diammonium polymer containing repeating units corresponding to the formula:

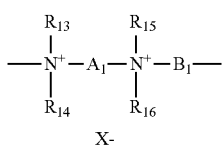

(IX)

in which formula (IX):

R13, R14, R15, and R16, which may be identical or different, represent aliphatic, alicyclic or arylaliphatic radicals containing from 1 to 20 carbon atoms or lower C1-C6 aliphatic hydroxyalkyl radicals, or alternatively R13, R14, R15, and R16, together or separately, constitute, with the nitrogen atoms to which they are attached, heterocycles optionally comprising a second heteroatom other than nitrogen, or alternatively R13, R14, R15, and R16 represent a linear or branched C1-C6 alkyl radical substituted with a nitrile, ester, acyl, or amide group or a group —CO—O—R17-D or —CO—NH—R17-D where R17 is an alkylene and D is a quaternary ammonium group;

A1 and B1 represent polymethylene groups comprising from 2 to 20 carbon atoms, which groups may be linear or branched, saturated or unsaturated, and which may comprise, linked to or intercalated in the main chain, at least one aromatic ring or at least one oxygen or sulphur atom or sulphoxide, sulphone, disulphide, amino, alkylamino, hydroxyl, quaternary ammonium, ureido, amide or ester group, and X— denotes an anion derived from a mineral or organic acid;

A1, R13 and R15 can form, with the two nitrogen atoms to which they are attached, a piperazine ring; in addition, if A1 denotes a linear or branched, saturated or unsaturated alkylene or hydroxyalkylene radical, B1 can also denote a group (CH2)n—CO-D-OC—(CH2)p- wherein:

n and p, which may be identical or different, are integers chosen from 2 to 20,

D denotes:

a) a glycol residue of formula: —O—Z—O—, wherein Z denotes a linear or branched hydrocarbon-based radical or a group corresponding to one of the following formulae:

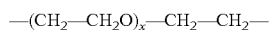

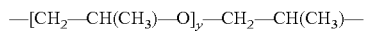

wherein x and y denote an integer chosen from 1 to 4, representing a defined and unique degree of polymerization, or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

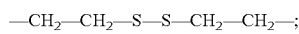

d) a ureylene group of formula: —NH—CO—NH—.

In at least one embodiment, X— is an anion such as chloride or bromide.

These polymers generally have a number-average molecular weight ranging from 1,000 to 100,000.

Polymers of this type are described for example in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may for example be made of polymers that are generally constituted of repeating units corresponding to those of formula (a):

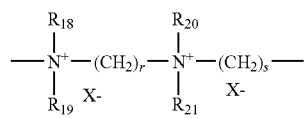

(a)

wherein $R_{18}$, $R_{19}$, $R_{20}$, and $R_{21}$, which may be identical or different, denote an alkyl or hydroxyalkyl radical having from 1 to 4 carbon atoms, r and s are integers chosen from 2 to 20, and X" is an anion derived from a mineral or organic acid.

One compound of formula (a) that may for example be used is the one for which $R_{18}$, $R_{19}$, $R_{20}$, and $R_{21}$ represent a methyl radical and r=3, s=6, and X=Cl, which is known as Hexadimethrine chloride according to the INCI (CTFA) nomenclature.

Family (5) polymers include polyquaternary ammonium polymers constituted of units of formula (X):

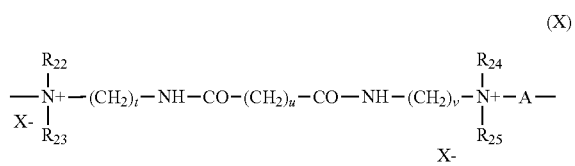

(X)

wherein:

R22, R23, R24, and R25, which may be identical or different, represent a hydrogen atom or a methyl, ethyl, propyl, β-hydroxyethyl, β-hydroxypropyl, or —CH2CH2(OCH2CH2)pOH radical, wherein p is equal to 0 or to an integer chosen from 1 to 6, with the proviso that R22, R23, R24, and R25 do not simultaneously represent a hydrogen atom, t and u, which may be identical or different, are integers chosen from 1 to 6, v is equal to 0 or to an integer chosen from 1 to 34, X— denotes an anion such as a halide, and A denotes a dihalide radical or for example represents —CH2-CH2-O—CH2-CH2-.

Such compounds are described for instance in patent application EP-A-122 324.

Examples that may be mentioned, in a non-limiting manner, include the products MIRAPOL® A15, MIRAPOL® AD1, MIRAPOLO AZ1 and MIRAPOL® 175 sold by the company Miranol.

Other cationic polymers that can be used in the context of the process disclosed herein are polyalkyleneimines, for example polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the process disclosed herein, cationic cyclopolymers may for example be used, for example the dimethyldiallylammonium chloride homopolymers sold under the name MERQUAT 100 by the company Nalco (and its homologues of low weight-average molar mass), and polyethyleneimines, and mixtures thereof.

According to the process disclosed herein, the at least one cationic polymer having a cationic charge density of greater than 4 meq/g may be present in an amount ranging from 0.001% to 10% by weight, for example from 0.005% to 5% by weight, such as from 0.01% to 3% by weight, relative to the total weight of the final composition.

According to at least one embodiment, the at least one dyeing composition may further comprise at least one non-ionic oxyalkylenated or glycerolated surfactant.

The expression "oxyalkylenated or glycerolated surfactant" is understood, within the context of the present disclosure, to mean a compound comprising at least one hydrocarbon-based chain comprising at least 6 carbon atoms and at least one group of structure:

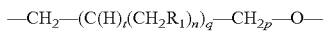

$$-CH_2-(C(H)_t(CH_2R_1)_n)_q-CH_{2p}-O-$$

wherein n or p or q denote, independently of one another, 0 or 1;

t denotes 1 or 2; and $R_1$ denotes a hydrogen atom or a hydroxyl radical.

These groups may be said to be oxyethylenated (q=0, p=1), oxypropylenated (q=1, n=0, t=2, p=1 or q=1, t=1, n=1, $R_1$=H) or glycerolated (q=1, n=0, t=2, p=1 or q=1, t=1, n=1, $R_1$=OH).

For example, the at least one non-ionic oxyalkylenated or glycerolated surfactant may be chosen from:

oxyalkylenated or glycerolated fatty alcohols;
oxyalkylenated alkylphenols, the alkyl chain of which is a $C_8$-$C_{18}$ alkyl chain;
oxyalkylenated or glycerolated fatty amides;
oxyalkylenated plant oils;
oxyalkylenated sorbitan esters of $C_6$-$C_{30}$ acids;
oxyalkylenated sucrose esters of fatty acids;
polyethylene glycol esters of fatty acids;
copolymers of ethylene oxide and of propylene oxide; and mixtures thereof.

In at least one embodiment, the average number of oxyalkylenated units ranges for example from 2 to 150 units. In another embodiment, they are oxyethylenated or oxypropylenated units or mixtures thereof.

As regards the glycerolated surfactants, they may for example comprise, on average, from 1 to 20 glycerol groups and for instance from 1.5 to 5.

In accordance with at least one embodiment of the process disclosed herein, the at least one dyeing composition comprises at least one non-ionic surfactant chosen from oxyalkylenated or glycerolated $C_6$-$C_{30}$ alcohols.

According to at least one embodiment of the process described herein, the total content of oxyalkylenated or glycerolated non-ionic surfactants present in the at least one dyeing composition ranges from 0.01% to 50% by weight, relative to the weight of the at least one dyeing composition, and for example from 0.1% to 30% by weight, such as from 0.1% to 20% by weight, such as from 0.1% to 10% by weight, relative to the weight of the at least one dyeing composition.

The at least one dyeing composition may also contain at least one direct dye which may for example be chosen from nitrobenzene dyes, azo direct dyes, methine direct dyes, and the addition salts thereof. The at least one direct dye may be of non-ionic, anionic, or cationic nature.

The at least one dyeing composition may comprise, in addition, at least one oxidizing agent.

Such an oxidizing agent may for example be chosen from hydrogen peroxide, urea peroxide, alkali metal bromates, ferricyanides, and persalts such as perborates and persulphates. Use may also be made, as an oxidizing agent, of at least one redox enzyme such as laccases, peroxidases, and 2-electron oxidoreductases (such as uricase), optionally in the presence of the respective donor or cofactor thereof.

Hydrogen peroxide may for example be used. This oxidizing agent may for example be constituted by an aqueous hydrogen peroxide solution, the titer of which may vary, for instance, from 1 to 40 volumes, and for example from 5 to 40 volumes.

The medium suitable for the dyeing, also known as a dye support, may be a cosmetic medium generally comprising water or a mixture of water and at least one organic solvent that is acceptable from a cosmetic point of view.

As examples of organic solvents, non-limiting mention may for example be made of solvents, for instance alcohols such as ethyl alcohol, isopropyl alcohol, benzyl alcohol and phenylethyl alcohol, or glycols or glycol ethers such as, for example, ethylene glycol monomethyl, monoethyl and monobutyl ethers, propylene glycol or its ethers such as, for example, propylene glycol monomethyl ether, butylene glycol, hexylene glycol, dipropylene glycol and also diethylene glycol alkyl ethers such as, for example, diethylene glycol monoethyl ether or monobutyl ether. The solvents may then be present in amounts ranging from 0.01% to 35% by weight and, for example, from 0.1% to 25% by weight relative to the total weight of the at least one dyeing composition.

The at least one dyeing composition may further comprise at least one adjuvant conventionally used in hair dyeing compositions.

The term "adjuvant" is understood to mean an additive, different from the aforementioned compounds.

As examples of adjuvants that can be used, non-limiting mention may be made of anionic surfactants, cationic surfactants, non-ionic surfactants other than those described previously, amphoteric surfactants, zwitterionic surfactants or mixtures thereof; anionic polymers, cationic polymers other than those described previously, non-ionic polymers, amphoteric polymers, zwitterionic polymers, or mixtures thereof; mineral or organic thickening agents, and for example anionic, cationic, non-ionic and amphoteric polymeric associative thickeners; antioxidants or reducing agents; penetrating agents; sequestering agents; fragrances, buffers, dispersing agents; conditioning agents such as, for example, volatile or non-volatile silicones, which may be modified or unmodified, and that are different from the organic silicon compounds disclosed herein; film-forming agents; ceramides, preservatives; opacifiers; and antistatic agents.

The above adjuvants are, in general, present in an amount ranging, for each of them, from 0.01% to 20% by weight, relative to the weight of the at least dyeing composition.

Of course, those skilled in the art will take care to select the optional adjuvant(s) mentioned above in such a way that the beneficial properties intrinsically associated with the compositions according to the process disclosed herein are not, or not substantially, impaired by the addition(s) envisaged.

The pH of the at least one dyeing composition generally ranges in value from 3 to 12, such as from 5 to 11 approximately. It may be adjusted to the desired value using acidifying or alkalinizing agents customarily used in hair dyeing or else with the aid of conventional buffer systems.

Among the alkalinizing agents, non-limiting mention may be made, by way of example, of aqueous ammonia, alkali metal carbonates, alkanolamines such as mono-, di- and triethanolamines and also derivatives thereof, oxyethylenated and/or oxypropylenated ethylenediamines and hydroxyalkylamines, sodium or potassium hydroxides and compounds of formula (XI) below:

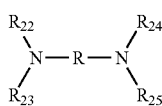

(XI)

wherein:
R is a propylene residue optionally substituted with a hydroxyl group or a $C_1$-$C_4$ alkyl radical;
$R_{22}$, $R_{23}$, $R_{24}$, and $R_{25}$, which are identical or different, represent a hydrogen atom, a $C_1$-$C_4$ alkyl radical, or $C_1$-$C_4$ hydroxyalkyl radical.

Among the acidifying agents, non-limiting mention may be made, by way of example, of mineral or organic acids such as hydrochloric acid, orthophosphoric acid, carboxylic acids such as tartaric acid, citric acid, lactic acid, or sulphonic acids.

The at least one dyeing composition may be in various forms, such as in the form of liquids, creams, gels, or in any other suitable form for dyeing hair.

The process disclosed herein is a process in which, in at least one embodiment, the at least one dyeing compition is applied to the hair fibers, without oxidizing agent, as defined previously, and the color is developed using at least one oxidizing agent. The color may be developed at acid, neutral, or alkaline pH and the at least one oxidizing agent may be added to the at least one dyeing composition just at the moment of use or it may be used starting from an oxidizing composition comprising it, applied simultaneously with or sequentially to the at least one dyeing composition disclosed herein. For example, this coloration may be developed at neutral pH.

According to at least one embodiment, the at least one dyeing composition without oxidizing agent is mixed, for example at the moment of use, with a composition containing, in a medium that is suitable for dyeing, at least one oxidizing agent. The mixture obtained is then applied to the hair. After a leave-in time that generally varies from 1 to 60 minutes, such as from 5 to 45 minutes, the hair is rinsed, optionally washed with shampoo, and rinsed again. The hair may optionally be dried.

The dyeing process disclosed herein comprises a post-treatment comprising applying, to the hair, at least one aqueous composition comprising at least one organic silicon compound as defined herein. The at least one aqueous composition comprising the at least one organic silicon compound thus applied may or may not be rinsed after an optional leave-in time. The hair may then be dried.

For example, the leave-in time of the at least one aqueous composition comprising the at least one organic silicon compound may range from a few seconds to 60 minutes, for example from 30 seconds to 15 minutes, such as from 1 minute to 5 minutes.

In at least one embodiment, the process disclosed herein comprises rinsing the hair after post-treating the hair via applying to the hair the at least one aqueous composition comprising the at least one organic silicon compound described herein.

Also disclosed herein is a multi-compartment device or "kit" for dyeing, comprising:
a first compartment containing at least one dyeing composition comprising at least one dyeing precursor,
a second compartment containing at least one oxidizing agent, and
a third compartment containing at least one aqueous composition comprising at least 30% of water and at least 20% of at least one organic silicon compound chosen from the silanes that comprise one silicon atom and the siloxanes that comprise two or three silicon atoms, wherein the at least one organic silicon compound comprises at least one basic chemical functional group and at least one hydroxyl group or hydrolysable group per molecule.

This device may be equipped with a device for applying the desired mixture to the hair, such as the devices described in patent FR-A-2 586 913.

Also disclosed herein is a method for making an aqueous composition for post-treating hair comprising combining water and at least one organo silicon compound chosen from the silanes that comprise one silicon atom and the siloxanes that comprise two or three silicon atoms,
wherein the at least one organic silicon compound also comprises at least one basic chemical functional group and at least one hydroxyl group or hydrolysable group per molecule,
wherein the water comprises at least 30% and the at least one organic silicon compound comprises at least 20% of the at least one aqueous composition, and
wherein the ingredients can be added in any order.

The following examples, without being limiting in nature, illustrate the embodiments disclosed herein.

EXAMPLE 1

The following compositions were produced (amount in grams of active material):
Aqueous Composition A, Containing at Least One Organic Silicon Compound:

| | |
|---|---|
| Lactic acid | 10.8 |
| Hydroxyethyl cellulose (Natrosol 250 HHR from Aqualon) | 0.4 |
| 3-Aminopropyltriethoxysilane Dow Corning Z-6011 Silane | 30 |
| Water | qs for 100 |

Composition B, Containing Oxidation Dyes and an Alkaline Agent:

| | |
|---|---|
| Oleic acid | 2.7 |
| Ammonium hydroxide | 2.22 (expressed as $NH_3$) |
| Pentasodium pentetate | 0.8 |
| Monoethanolamine | 0.63 |
| 2-Oleamido-1,3-octadecanediol | 0.01 |
| 2,5-Diaminotoluene | 0.7623 |
| Resorcinol | 0.66 |
| m-Aminophenol | 0.14 |
| 2,4-Diaminophenoxyethanol 2HCl | 0.02 |
| Cetearyl alcohol | 16.2 |
| Oleyl alcohol | 2.7 |
| Hexadimethrine chloride (Mexomer PO from Chimex) | 3 |
| Oleth-30 | 3.6 |
| Sodium metabisulphite | 0.71 |
| Fragrance | 0.5 |
| Water | qs for 100 |

Composition C, Containing Aqueous Hydrogen Peroxide:

| | |
|---|---|
| Trideceth Carboxamide Mea | 0.85 |
| Sodium stannate | 0.04 |
| Pentasodium pentetate | 0.06 |
| Glycerol | 0.5 |
| Cetearyl alcohol | 2.28 |
| Ceteareth-25 | 0.57 |

| | |
|---|---|
| Hydrogen peroxide | 6 |
| Tetrasodium pyrophosphate | 0.02 |
| Phosphoric acid | qs for pH 2 |
| Water | qs for 100 |

Composition B, containing oxidation dyes, was diluted extemporaneously with 1 and a half times its weight of Composition C, comprising the oxidizing agent.

The mixture thus produced was applied to fine chestnut hair. After waiting for 30 minutes, the hair was rinsed, and washed with standard shampoo.

Next, as a post-treatment to the dyeing, Composition A, comprising (3-aminopropyl)triethoxysilane, was applied to the hair.

After waiting for 5 minutes, the hair was rinsed.
Following the above lightening and dyeing, hair dyed a light chestnut color was in the end obtained. The hair had pronounced styling properties with increased volume and body.

What is claimed is:

1. A hair dyeing process comprising,
   (a) dyeing the hair by a process comprising
      applying to the hair at least one dyeing composition comprising at least one dye precursor, and
      rinsing the hair; and
   (b) post-treating the hair by a process comprising
      applying to the hair at least one aqueous composition comprising at least 30% of water and at least 20% of at least one organic silicon compound chosen from the silanes that comprise one silicon atom and the siloxanes that comprise two or three silicon atoms, wherein the at least one organic silicon compound also comprises at least one basic chemical functional group and at least one hydroxyl group or hydrolysable group per molecule.

2. The hair dyeing process according to claim 1, wherein the at least one organic silicon compound comprises at least one basic chemical functional group chosen from primary, secondary, and tertiary amines.

3. The hair dyeing process according to claim 1, wherein the at least one organic silicon compound comprises at least one hydrolysable group chosen from alkoxy, aryloxy, and halogen groups.

4. The hair dyeing process according to claim 1, wherein the at least one organic silicon compound is chosen from those of formula (I):

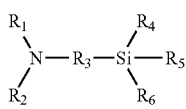

(I)

wherein:
$R_4$ represents a halogen or an OR' or $R'_1$, group;
$R_5$ represents a halogen or an OR'' or $R'_2$ group;
$R_6$ represents a halogen an OR''' or $R'_3$ group;
$R_1, R_2, R_3, R', R'', R''', R'_1, R'_2$, and $R'_3$ represent, independently of one another, a saturated or unsaturated, linear or branched hydrocarbon-based group optionally bearing additional chemical groups, $R_1, R_2, R', R''$, and $R'''$ optionally being hydrogen, and at least two of the groups $R_4, R_5$, and $R_6$ respectively denoting OR', OR'', and OR''', at least two of the groups R', R'', and R''' being other than hydrogen;

and from those of formula (II):

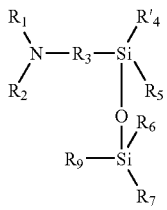

(II)

wherein:
$R_1, R_2, R_3, R_5$, and $R_6$ are defined as above;
$R'_4$ represents a halogen atom or an $OR_{11}$ group;
$R_7$ represents a halogen atom or an $OR_{10}$ or $R''_1$ group;
$R_9$ represents a halogen atom an $OR_8$, $R''_2$, or $R_3NR_1R_2$ group; and
$R''_1, R''_2, R_8, R_{10}$, and $R_{11}$ represent a saturated or unsaturated, linear or branched hydrocarbon-based group optionally bearing additional chemical groups, the groups $R_{11}, R_{10}$, and $R_8$ optionally representing a hydrogen atom; at least one of the groups $R_6, R_7$, and $R_9$ denoting a halogen atom or an OR''', $OR_{10}$, or $OR_8$) group.

5. The hair dyeing process according to claim 4, wherein the groups $R_1, R_2, R', R'_1, R'_2, R'_3, R'', R''', R''_1, R''_2, R_8, R_{10}$, and $R_{11}$ are chosen from $C_1$-$C_{12}$ alkyl, $C_6$ to $C_{14}$ aryl, ($C_1$ to $C_8$)alkyl($C_6$ to $C_{14}$)aryl, and ($C_6$ to $C_{14}$)aryl($C_1$ to $C_8$)alkyl radicals.

6. The hair dyeing process according to claim 1, wherein the at least one organic silicon compound is chosen from those of formula (III):

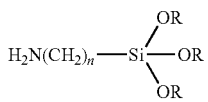

(III)

wherein the R radicals, which are identical or different, are chosen from $C_1$-$C_6$ alkyl radicals and n is an integer chosen from 1 to 6.

7. The hair dyeing process according to claim 6, wherein n is an integer chosen from 2 to 4.

8. The hair dyeing process according to claim 1, wherein the at least one organic silicon compound is (3-aminopropyl)triethoxysilane.

9. The hair dyeing process according to claim 1, wherein the at least one organic silicon compound is present in an amount ranging from 20% to 65%, relative to the total weight of the at least one aqueous composition.

10. The hair dyeing process according to claim 9, wherein the at least one organic silicon compound is present in an amount ranging from 30% to 60%, relative to the total weight of the at least one aqueous composition.

11. The hair dyeing process according to claim 1, wherein the water is present in an amount ranging from 30% to 78%, relative to the total weight of the at least one aqueous composition.

12. The hair dyeing process according to claim 11, wherein the water is present in an amount ranging from 40% to 70%, relative to the total weight of the at least one aqueous composition.

13. The hair dyeing process according to claim 1, wherein the at least one dye precursor is chosen from at least one oxidation base and/or at least one coupler.

14. The hair dyeing process according to claim 1, wherein the at least one dyeing precursor is chosen from:
- at least one oxidation base chosen from ortho-phenylenediamines and para-phenylenediamines, double bases, ortho-aminophenols and para-aminophenols, heterocyclic bases, and the addition salts thereof with an acid; and/or
- at least one coupler chosen from meta-aminophenols, meta-phenylenediamines, meta-diphenols, naphthols, heterocyclic couplers, and the addition salts thereof with an acid.

15. The hair dyeing process according to claim 1, wherein the at least one dyeing composition further comprises at least one cationic polymer, the cationic charge density of which is greater than or equal to 4 meq/g.

16. The hair dyeing process according to claim 1, wherein the at least one dyeing composition further comprises at least one polyoxyethylene or glycerolated non-ionic surfactant.

17. The hair dyeing process according to claim 1, wherein the dyeing is carried out in the presence of at least one oxidizing agent.

18. The hair dyeing process according to claim 17, wherein the at least one oxidizing agent is hydrogen peroxide.

19. A method for making an aqueous composition for post-treating hair comprising combining water and at least one organo silicon compound chosen from the silanes that comprise one silicon atom and the siloxanes that comprise two or three silicon atoms,
- wherein the at least one organic silicon compound also comprises at least one basic chemical functional group and at least one hydroxyl group or hydrolysable group per molecule,
- wherein the water comprises at least 30% and the at least one organic silicon compound comprises at least 20% of the at least one aqueous composition, and
- wherein the ingredients can be added in any order.

20. A multicompartment device or kit for dyeing hair comprising:
- a first compartment containing at least one dyeing composition comprising at least one dye precursor,
- a second compartment containing at least one oxidizing agent, and
- a third compartment containing at least one aqueous composition comprising at least 30% of water and at least 20% of at least one organic silicon compound chosen from the silanes that comprise one silicon atom and the siloxanes that comprise two or three silicon atoms, wherein the at least one organic silicon compound also comprises at least one basic chemical functional group and at least one hydroxyl group or hydrolysable group per molecule.

* * * * *